(12) United States Patent
Auerswald et al.

(10) Patent No.: US 8,043,490 B2
(45) Date of Patent: Oct. 25, 2011

(54) ELECTROCHEMICAL SENSOR

(75) Inventors: Lothar Auerswald, Döbeln (DE);
Christian Fanselow, Geringswalde (DE)

(73) Assignee: Endress+ Hauser Conducta Gesellschaft für Mess- und Regeltechnik mbH+ Co. KG, Gerlingen (DE)

( * ) Notice: Subject to any disclaimer, the term of this patent is extended or adjusted under 35 U.S.C. 154(b) by 316 days.

(21) Appl. No.: 12/226,270

(22) PCT Filed: Mar. 21, 2007

(86) PCT No.: PCT/EP2007/052695
§ 371 (c)(1),
(2), (4) Date: May 18, 2009

(87) PCT Pub. No.: WO2007/118753
PCT Pub. Date: Oct. 25, 2007

(65) Prior Publication Data
US 2009/0301874 A1    Dec. 10, 2009

(30) Foreign Application Priority Data
Apr. 13, 2006   (DE) .......................... 10 2006 017 981

(51) Int. Cl.
*G01N 27/333* (2006.01)
(52) U.S. Cl. ........ 204/420; 204/416; 204/435; 204/433; 205/787.5
(58) Field of Classification Search ............... 204/416, 204/420, 433, 435; 205/787.5; 324/450
See application file for complete search history.

(56) References Cited

U.S. PATENT DOCUMENTS

| | | | |
|---|---|---|---|
| 4,012,308 A | 3/1977 | Jerrold-Jones | |
| 4,128,468 A | 12/1978 | Bukamier | |
| 4,162,211 A | 7/1979 | Jerrold-Jones | |
| 4,608,148 A | 8/1986 | Frollini | |
| 4,814,058 A * | 3/1989 | Bordenick | 204/401 |
| 5,830,338 A * | 11/1998 | Seto et al. | 204/416 |

FOREIGN PATENT DOCUMENTS
EP        0 076 464       4/1983
* cited by examiner

*Primary Examiner* — Jeffrey T Barton
*Assistant Examiner* — Maris R Kessel
(74) *Attorney, Agent, or Firm* — Bacon & Thomas, PLLC

(57) ABSTRACT

A combination electrode, including: A first tube; a measuring membrane, which sealedly closes the first tube to form a measuring chamber; a second tube, which surrounds the first tube and is connected borderingly with the first tube to form an annular reference chamber; a buffer solution located in the measuring chamber; an electrolyte solution located in the reference chamber; a first tapping electrode in contact with the buffer solution; and a second tapping electrode in contact with the electrolyte; wherein, additionally, arranged in the reference chamber is an axially shiftable, annular, sealing element, which bounds the volume occupied by the electrolyte solution, the sealing element is biased by means of an electrically conductive, elastic, deformation element, which surrounds the first tube, and the second tapping electrode is electrically connected with the deformation element, in order to tap the potential of the second electrode via the deformation element.

11 Claims, 3 Drawing Sheets

ELECTROCHEMICAL SENSOR

TECHNICAL FIELD

The present invention relates to an electrochemical sensor, especially a potentiometric sensor, for example, a pH-sensor. An established embodiment of this kind of sensor is a combination electrode, which finds broad application for electrochemical measuring and control of pH-values in many fields of chemistry, environmental analytics, medicine, industry and water management. Combination electrodes include, assembled, a working electrode and a reference element.

BACKGROUND DISCUSSION

Used as reference element is, for example, a silver/silver-chloride electrode, which reaches into a reference electrolyte, for example, KCl, located in an annular chamber around the working electrode. The reference electrolyte can be present, for example, as liquid and/or as gel. The working, or measuring, electrode comprises, usually, a glass tube, which is closed with a glass-membrane facing toward the medium to be measured and filled with a buffer solution. The electrode wire reaches into the buffer solution.

Insofar as the glass-membrane has a very high impedance, the measured potential is very disturbance-susceptible, so that it should, as much as possible, be well shielded.

The reference electrolyte in the annular chamber surrounding the measuring electrode is, in certain respects, suitable as shielding; however, it has, for example, a temperature-dependently variable volume, so that an air chamber can form above the reference electrolyte, surrounding the measuring electrode, whereupon the measuring electrode is not sufficiently shielded in the axial section of the air chamber.

FIG. 3 shows, for purposes of explanation, a combination electrode 61 of the state of the art, which has, between an outer tube 62 and an inner tube 63, an annular reference chamber 64, which is filled with a reference electrolyte. The reference potential is tapped with a reference electrode wire 67, which extends through various seals in the axial direction in the reference chamber. In the upper end of the reference chamber 64 is a so-called compensator 74, which comprises a closed-pore, elastic foam. The foam of the compensator is pressure-dependently compressed, so that, within a working range of the foam, the variable volume of the reference electrolyte can be accommodated. Above the compensator are a silicone caulking 78 and an epoxide resin caulking 79. The described apparatus is disadvantageous for the following reasons. On the one hand, the volume accommodated by the limited compressibility of the foam is limited, and, on the other hand, the volume of the foam cannot be arbitrarily increased, since, in the area of the foam, no effective shielding is provided. Furthermore, problems with sealing can be expected, since the foam moves relative to the reference electrode wire, and such movement can also affect the interface between the silicone caulking and the electrode wire.

SUMMARY OF THE INVENTION

It is, therefore, an object of the invention to provide a combination electrode overcoming the disadvantages of the state of the art.

The object is achieved according to the invention by a combination electrode which includes: A first tube, which is electrically non-conductive, at least in the radial direction; a measuring membrane, which is arranged on a first end section of the first tube and sealedly closes the first tube to form a measuring chamber; a second tube, which, at least sectionally, surrounds the first tube and is, directly or indirectly, connected with the first tube, so that, between the first tube and the second tube, an annular reference chamber is formed; a buffer solution located in the measuring chamber; an electrolyte solution located in the reference chamber; a first electrode in contact with the buffer solution, in order to tap a first potential; and a second electrode in contact with the electrolyte, in order to tap a second potential; wherein arranged additionally in the reference chamber is an annular sealing element, which is axially shiftable in the annular chamber and bounds, in the axial direction, the volume occupied by the electrolyte solution; wherein the sealing element is axially biased by means of an electrically conductive, elastic, deformation element surrounding the first tube, and the second electrode is electrically conductively connected with the deformation element, so that the potential of the second electrode can be tapped via the deformation element.

The elastic deformation element serves preferably as electrical shielding for the axial section of the first electrode surrounded by the deformation element.

In an embodiment of the invention, the second electrode is secured with an end section on the sealing element, and moves, at least sectionally, with the sealing element in the axial direction in the reference container.

In an embodiment of the invention, the combination electrode further includes an annular support element, which is fixedly connected with the first and/or second tube in an end section of the reference chamber away from the first end section of the first or second tube, wherein the elastic deformation element is axially clamped between the support element and the sealing element. The support element can, furthermore, close the reference chamber.

In a further development of the invention, the combination electrode further includes an electrically conductive, especially metal, tapping element for tapping the potential of the second electrode, wherein the tapping element is fixedly connected with the support element and is, directly or indirectly, in galvanic contact with the second electrode via the elastic deformation element. Preferably, the support element and/or the sealing element include(s) an electrically conductive material.

In a currently preferred embodiment of the invention, the electrolyte solution includes KCl and the second electrode comprises an Ag/AgCl-electrode. For lengthening the diffusion path of silver ions, which are dissolved in the reference electrolyte, and which could plug a diaphragm serving as a current-key between the reference electrolyte and a medium surrounding the combination electrode, the combination electrode includes, in an embodiment of the invention, a unilaterally closed, capillary tube, which is arranged in the reference chamber and in which the Ag/AgCl-electrode extends.

BRIEF DESCRIPTION OF THE DRAWINGS

The invention will now be explained on the basis of examples of embodiments illustrated in the drawing, the figures of which show as follows.

DETAILED DISCUSSION

Figure 1:
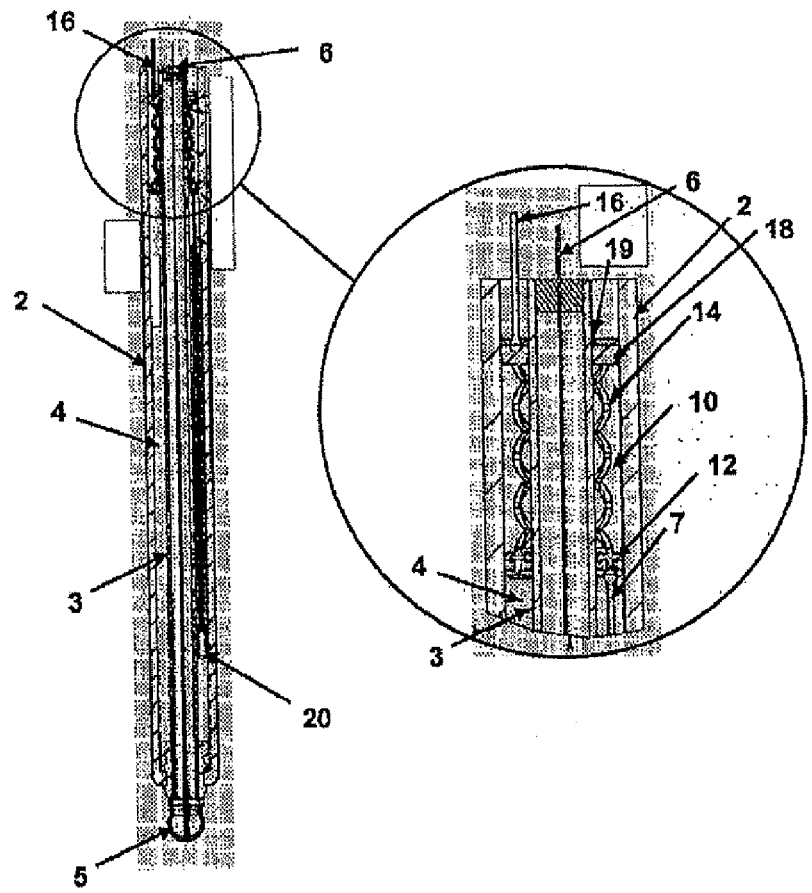
FIG. 1 a longitudinal section through a first embodiment of a combination electrode of the invention.

The combination electrode 1 of FIG. 1 includes an inner tube 3, which has, on a first end section, a pH glass-membrane 5, which closes the inner tube at the first end section. The inner tube with the pH glass-membrane 5 serves as measuring cell, or measuring chamber, and is filled, in measuring operation, with a buffer solution of pH 7. The pH-dependent, measurement potential is tapped via an electrode wire 6, which extends in the axial direction to a second end section of the inner tube 3 and then out through a feedthrough.

An outer tube 2 coaxially surrounds the inner tube and is connected with the inner tube in the region of the first end section, so that an annular chamber 4 is formed between the inner and outer tubes. The annular chamber is filled, in measurement operation, with a reference electrolyte, for example, 3N KCl, and serves as reference chamber, or reference cell, for the measuring chamber. The outer tube 2 has, additionally, a diaphragm in an outer wall, to serve as a so-called current-key of the reference cell.

Figure 2:
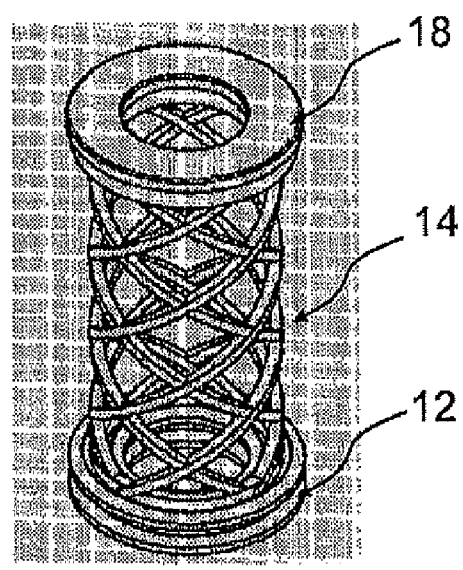
FIG. 2 a view of a deformation element of a combination electrode of the invention.
Figure 3:
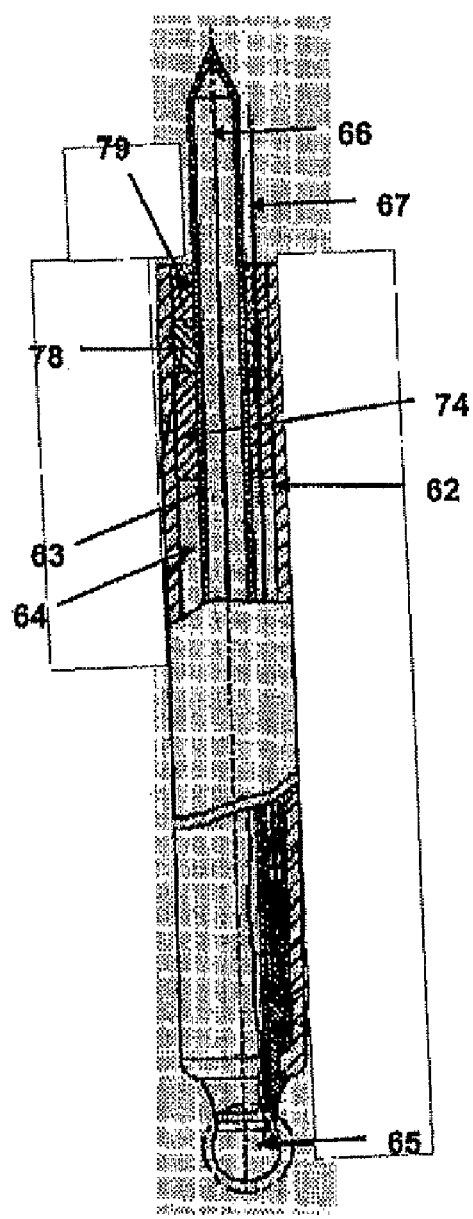
FIG. 3 a longitudinal section through a combination electrode of the state of the art discussed in the introduction.

In the second end section of the annular chamber 4, a pressure compensator is provided, which will now be explained using the detail in FIG. 1. The pressure compensator comprises a sealing ring 12, which is electrically conductive, at least in the axial direction. Sealing ring 12 is made, for example, of a metallized, synthetic material, or it is a metal sealing ring with elastic sealing lips, for example, of an organic material, wherein the underside of the sealing ring faces the reference electrolyte and is in contact with it. Secured in suitable manner on the underside of the sealing ring 12 is, furthermore, a silver wire 7 of the reference electrode. Wire 7 can, for example, be held adhered with a conductive adhesive, cast in, welded, shape-interlocked or with a clamped seating. Secured on the upper side of the sealing ring 12 is a conductive, elastic and axially flexible, spring basket 14, which is shown in detail in FIG. 2. Suitable materials for the spring basket include, for example, metals, as well as metallized elastomers and composite materials.

The basket structure provides an effective shielding of the axial section of the working electrode surrounded by the spring basket 14.

Secured on the upper end of the spring basket 14, away from the sealing ring 12, is an electrically conducting, sealing washer 18. As illustrated in FIG. 1, washer 18 is secured by means of adhesive layers on the outer tube 2 and the inner tube 3, so that washer 18 sealedly closes the annular chamber 4. Optionally, an air escape path (not shown) can be provided through the sealing washer 18, in order to enable a pressure equalization between the enclosed volume of an air chamber 10 above the sealing ring 12 and the environment of the combination electrode. This air escape path can, if desired, be provided in the form of a capillary path, and have protective means against liquid exchange, for example, a filter.

An electrically conductive, contact pin 16 is secured on the upper side of the sealing washer 18 in galvanic contact with the sealing washer. As a result, via the sealing ring 12, the spring basket 14 and the sealing washer 18, an electrically conducting connection is provided between the silver wire 7 of the reference electrode and the contact pin 16, for tapping the reference potential.

FIG. 1 shows, furthermore, a capillary tube 20, which is arranged in the annular chamber 4, and loosely surrounds the electrode wire 7, so that the electrode wire is sufficiently surrounded by the reference electrolyte. On the lower end of the electrode wire 7 is provided an AgCl-supply, in which the electrode wire ends. From there, dissolved silver ions can reach the diaphragm of the current-key by diffusion, with the diffusion path being lengthened by the capillary tube, in order to lengthen the service life of the sensor.

For preventing a pump effect by relative movements in the area of high silver ion concentration, it is provided in an embodiment of the invention, that the capillary tube 20 moves together with the electrode wire. To this end, it is mechanically coupled either with the sealing ring 12 or the electrode wire 7.

In another embodiment, the electrode wire can have, between the sealing element and the capillary tube, a flexible, wound section, which deforms in the case of axial shifting of the sealing element, so that axial shifting between the section of the second electrode in the capillary tube and the capillary tube are reduced, or prevented, in the case of axial shifting of the sealing element.

In an additional embodiment of the invention, instead of a spring basket, a usual, metal, helical spring is provided as elastic deformation element, wherein the end sections of the helical spring can, for example, be cast in a conductive sealing ring and/or a conductive sealing washer. Of course, other securements are possible.

Suitable material for the inner and outer tubes for implementing the invention include all established materials for combination electrodes, for example, glass or selected synthetic materials, such as PEEK.

The invention claimed is:

1. A combination electrode, comprising:
    a first tube, which is, at least radially, electrically non-conductive;
    a measuring membrane, which is arranged at a first end section of said first tube and which sealedly closes said first tube to form a measuring chamber;
    a second tube, which, at least sectionally, surrounds said first tube and which is connected with said first tube, so that, between said first tube and said second tube, an annular reference chamber is formed;
    a buffer solution located in said measuring chamber;
    an electrolyte solution located in said reference chamber;
    a first electrode in contact with said buffer solution, in order to tap a first potential;
    and a second electrode in contact with the electrolyte, in order to tap a second potential, wherein:
    arranged in said reference chamber is an annular sealing element, which is axially shiftable in said annular reference chamber and which axially bounds a volume occupied by the electrolyte solution; and
    said annular sealing element is axially biased by means of an electrically conductive, elastic, deformation element, which surrounds said first tube, and said second electrode is electrically conductively connected with said deformation element, so that the potential of said second electrode can be tapped via said deformation element.

2. The combination electrode as claimed in claim 1, wherein:
    said elastic deformation element serves as electrical shielding for a section of said first electrode.

3. The combination electrode as claimed in claim 1, wherein:
    the second electrode is secured with an end section to said sealing element and moves with the sealing element axially in said reference chamber.

4. The combination electrode as claimed in claim 1, further comprising:
    an annular support element, which is fixedly connected with said first and/or said second tube in an end section of said reference chamber, away from said first end section of said first or second tube, wherein:
    said elastic deformation element is axially clamped between said support element and said sealing element.

5. The combination electrode as claimed in claim 4, wherein:
said support element closes said reference chamber.

6. The combination electrode as claimed in claim 4, furthermore comprising:
a metal tapping element for tapping the second potential, wherein:
said tapping element is fixedly connected with said support element and galvanically connected with said second electrode.

7. The combination electrode as claimed in claim 4, wherein:
said support element comprises an electrically conductive material.

8. The combination electrode as claimed in claim 1, wherein:
said sealing element comprises an electrically conductive material.

9. The combination electrode as claimed in claim 1, wherein:
the electrolyte solution includes KCl, and said second electrode is an Ag/AgCl-electrode.

10. The combination electrode as claimed in claim 9, further comprising:
a unilaterally closed capillary tube, which is arranged in said reference chamber, and in which said second electrode extends, wherein:
said capillary tube is directly or indirectly coupled with said second electrode, for preventing relative movement.

11. The combination electrode as claimed in claim 9, further comprising:
a unilaterally closed capillary tube, which is arranged in said reference chamber, and in which said second electrode extends, wherein:
said second electrode comprises a wire, which, between said sealing element and said capillary tube, has a flexible, wound section, which deforms in the case of axial shifting of said sealing element, so that axial shifting between the section of said second electrode in said capillary tube and said capillary tube is reduced or prevented in the case of axial shifting of said sealing element.

* * * * *